United States Patent [19]

Snader et al.

[11] 4,025,614

[45] May 24, 1977

[54] SUBSTITUTED 2H-PYRAN-2,6 (3H)-DIONE DERIVATIVES USEFUL IN TREATMENT OF ALLERGIC REACTIONS

[75] Inventors: Kenneth M. Snader, Hatboro, Pa.; Chester R. Willis, Kingston, Jamaica

[73] Assignee: SmithKline Corporation, Philadelphia, Pa.

[22] Filed: Apr. 30, 1976

[21] Appl. No.: 681,945

[52] U.S. Cl. .............................. 424/45; 260/239.6; 260/345.9; 424/229; 424/283
[51] Int. Cl.² ...................... A01N 9/28; A61L 9/04; C07D 231/42; C07D 309/22
[58] Field of Search ..................... 260/239.6, 345.9; 424/283, 45, 229

[56] References Cited

OTHER PUBLICATIONS

J. Org. Chem. 21 686–688 (1956), Wiley et al.
J. Chem. Soc. (c) 2721–2726 (1971), Kiang et al.
Derwent Basic Abstract 12477X of Netherlands application No. 7509–032, Feb. 2, 1976.

Primary Examiner—Albert T. Meyers
Assistant Examiner—D. W. Robinson
Attorney, Agent, or Firm—Richard D. Foggio; William H. Edgerton

[57] ABSTRACT

Substituted 2H-pyran-2,6(3H)-dione derivatives useful in the treatment of allergic conditions are prepared by reaction of 3,5-diacetyl-4,6-dihydroxy-2H-pyran-2-one with an appropriate aniline.

15 Claims, No Drawings

SUBSTITUTED 2H-PYRAN-2,6 (3H)-DIONE DERIVATIVES USEFUL IN TREATMENT OF ALLERGIC REACTIONS

This invention relates to substituted 2H-pyran-2,6(3H)-dione derivatives which are useful for inhibiting the symptoms of an allergic response resulting from an antigen-antibody reaction. More specifically, the compounds of this invention are believed to be effective by inhibiting the release and/or formation and release of pharmacologically active mediators such as histamine, serotonin and slow-reacting substance of anaphylaxis (SRS-A) from effector cells which are produced and/or released as a result of an interaction of antigen and specific antibody fixed to the cell surface (allergic reaction). These properties make the subject compounds particularly useful in the treatment of various allergic diseases such as asthma, rhinitis and urticaria.

The compounds of this invention are represented by the following general structural formula:

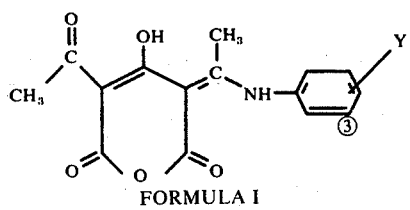

FORMULA I wherein Y represents sulfamyl, methylsulfonamido, phenylsulfonamido or sulfamido, preferably in the 3-position.

The compounds of formula I are conveniently prepared as shown in the following scheme:

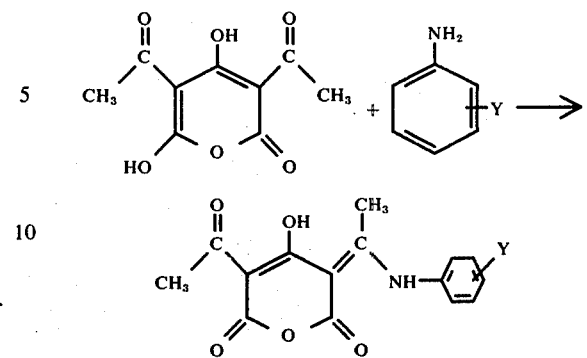

in which Y is as defined above. Thus, 3,5-diacetyl-4,6-dihydroxy-2H-pyran-2-one and the appropriately substituted aniline are heated at reflux in an inert organic solvent such as benzene, toluene, ethanol or methanol for from one to three hours to give the products. Advantageously, where Y is sulfamido, the reactants are combined in tetrahydrofuran at room temperature for from 18 to 48 hours.

Mono-and di-alkali metal salts of the compounds of of formula I, such as the mono-and di-sodium or potassium salts are readily obtainable by treatment with the appropriate alkali metal alkoxide, for example methoxide, in an alkanol solvent such as methanol.

The pyran-2-one starting material indicated above is obtained by reaction of acetonedicarboxylic acid with acetic anhydride in sulfuric acid at elevated temperature. The reaction product actually has the tautomeric structure as shown below:

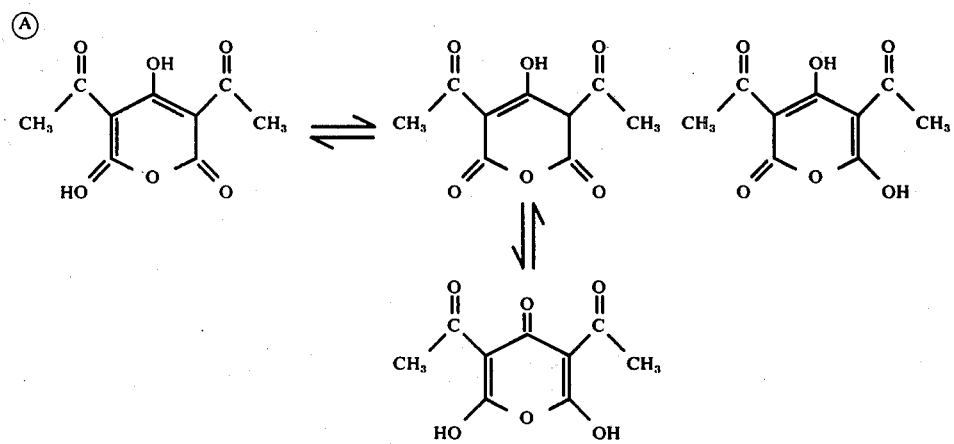

however for convenience it is designated herein as 3,5-diacetyl-4,6-dihydroxy-2H-pyran-2-one. Accordingly the reaction of this product with an aniline as shown above gives a product having the tautomeric structures as shown below:

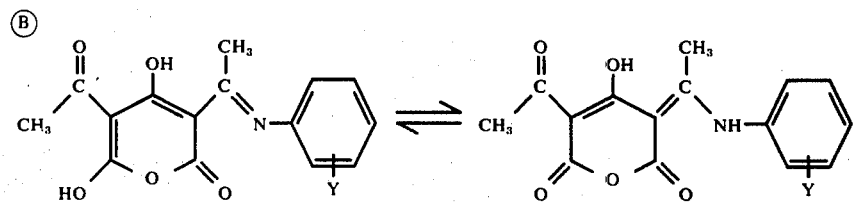

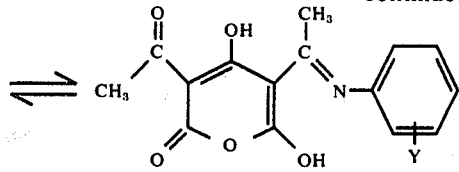

in which Y is as defined above for formula I. For convenience we have chosen to use one tautomeric form, namely the intermediate enamine pyran-2,6-dione structure, to represent all of the compounds formed by reaction of Ⓐ with the aniline, as indicated by formula I above. It will be apparent however to one skilled in the art that the more complete representation of the compounds of formula I is shown by the tautomerization Ⓑ.

The substituted aniline starting materials used herein are conveniently prepared by well-known preparative methods.

Wiley, R. H. et al. *J. Org. Chem.* 21:686–688 (1965) has reported the reaction of amines with the reaction product of acetonedicarboxylic acid and acetic anhydride, the latter designated 5-carboxydehydroacetic acid. Similarly, Kiang, A. K. et al. *J. Chem. Soc.* (c) pp. 2721–6 (1971) has disclosed such reaction products with amines. However there is no disclosure of products represented by formula I.

The inhibitory activity of the compounds of this invention on mediator release in sensitized tissues, thereby inhibiting the effects of the allergic reaction, is measured by the ability of the test compound to inhibit the passive cutaneous anaphylaxis (PCA) reaction in rats. In this test system, titered and appropriately diluted serum (from rats previously immunized by the intraperitoneal injection of ovalbuminaluminum hydroxide or ovalbumin-i.m.-Bordatella pertussis U.S.P. i.p.-and N-Brasiliensis i.p.) containing reaginic antibodies directed against ovalbumin is injected intradermally at four sites on the shaved backs of adult male rats. Forty-eight hours later the animals are injected intravenously with 0.5 ml. of isotonic saline solution containing 5 mg. of the ovalbumin antigen and 5 mg. of Evans blue dye. Chemical mediators such as histamine and serotonin which are released at the sensitized sites as a result of a local cellular anaphylaxis, cause an increase in capillary permeability with resultant leakage of plasma and formation of a wheal. The wheal is visualized by the plasma protein-bound Evans blue dye. Under conditions of the test, the average control wheal is approximately 12×12 mm. Thirty minutes following antigen challenge, the animals are killed, the dorsal skin is reflected and the diameter of the wheals recorded. A test compound is administered intravenously, initially at 0.5 minutes prior to antigen challenge (longer pretreatment times and other routes of drug administration, i.e. oral or intraperitoneal, may be employed). Percent inhibition is calculated from the difference in mean average wheal diameter between a treated group and saline or appropriate diluent controls.

The interruption by a test compound of the sequence of events triggered by reaginic antibody-antigen interaction on the surface of sensitized cells is indicative of utility in inhibiting the symptoms which result from an immediate-type allergic response.

The compounds of formula I administered intravenously to rats at doses of from 0.25 to 10 mg/kg produce marked inhibition of the PCA reaction. For example, 5-acetyl-4-hydroxy-3-[1-(3-sulfamidophenylamino)ethylidene]-2H-pyran-2,6(3H)-dione produced 35% inhibition of the rat PCA wheal at 0.25 mg/kg, i.v. Another compound, 5-acetyl-4-hydroxy-3-[1-(3-sulfamylphenylamino)ethylidene]-2H-pyran-2,6(3H)-dione, produced 45% inhibition of the rat PCA wheal at 0.5 mg/kg, i.v.

In testing for mechanism of action the compounds of formula I, following i.v. administration at the same dose and pretreatment time which exhibited significant inhibition of the rat 48-hour PCA reaction, do not provide comparable inhibition of wheals of equal severity produced in rats by the intracutaneous administration of histamine and serotonin.

The compounds of this invention may be administered in conventional pharamaceutical compositions comprising an appropriate amount of a compound of formula I in association with a pharmaceutical carrier or diluent. The nature of the composition and the pharmaceutical carrier or diluent will of course depend upon the intended route of administration, i.e. orally, parenterally or by inhalation. Preferably a compound is administered to an animal in a composition comprising an amount sufficient to produce an inhibition of the symptoms of an allergic response. When employed in this manner, the dosage of the composition is such that from 2.5 mg. to 500 mg. of active ingredient are administered at each administration. Advantageously equal doses will be administered 1 to 4 times daily with the daily dosage regimen being about 2.5 mg. to about 2000 mg.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant such as dichlorodifluoromethane or chlorotrifluoroethane to be administered from a pressurized container. The compositions may also comprise the solid active ingredient diluted with a solid diluent, e.g. lactose, for administration from a powder inhalation device. In the above compositions, the amount of carrier or diluent will vary but preferably will be the major proportion of a suspension or solution of the active ingredient. When the diluent is a solid, it may be present in less, equal or greater amounts than the solid active ingredient.

A wide variety of other pharmaceutical forms can be employed. Thus, if a solid carrier is used the preparation can be tableted, placed in a hard gelatin capsule in powder or pellet form, or in the form of a troche or lozenge for oral administration. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampul, or an aqueous or non-aqueous liquid suspension.

Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

The pharmaceutical preparations thus described are made following the conventional techniques of the pharmaceutical chemist involving mixing, granulating and compressing when necessary, or variously mixing and dissolving the ingredients as appropriate to the desired end product.

Included within the scope of this invention is the method of inhibiting the symptoms of an allergic response resulting from an antigen-antibody reaction which comprises administering to an animal a therapeutically effective amount for producing said inhibition of a compound of formula I, preferably in the form of a pharmaceutical composition. The administration may be carried out in dosage units at suitable intervals or in single doses as needed. Preferably the method of this invention is practiced when relief of allergic symptoms is specifically required, however, the method is also usefully carried out as continuous or prophylactic treatment. A particular application is a method of relieving or preventing allergic airway obstruction which comprises administering to an animal a therapeutically effective amount at suitable intervals. It is within the skill of the art to determine by routine experimentation the effective dosage to be administered from the dose range set forth above, taking into consideration such factors as the degree of severity of the allergic condition being treated, and so forth.

The following examples illustrate the preparation of compounds of formula I and their incorporation into pharmaceutical compositions and as such are not to be considered as limiting the invention set forth in the claims appended hereto.

EXAMPLE 1

To a solution of 2.76 g. (0.02 mol) of m-nitroaniline in 5 ml. of pyridine cooled to 0° C. is added 1.6 ml. (0.02 mol) of methanesulfonyl chloride dropwise and the mixture is stirred at room temperature for two hours. The reaction mixture is decomposed by addition of dilute hydrochloric acid and ice, and dried to give m-(methylsulfonamido)-nitrobenzene, m.p. 237° C. The latter, 1.08 g. (0.005 mol), is dissolved in 100 ml. of ethanol, 300 mg. of 10% palladium-on-carbon is added and the mixture is hydrogenated in a Parr shaker. After hydrogen uptake has ceased, the catalyst is filtered off leaving the product, 3-methylsulfonamidoaniline, in solution. To this solution (100 ml. ethanol) is added 1.08 g. (0.005 mol) of 3,5-diacetyl-4,6-dihydroxy-2H-pyran-2-one and the solution is refluxed for one hour. The reaction mixture is concentrated and filtered to yield 5-acetyl-4-hydroxy-3-[1-(3-methylsulfonamidophenylamino)ethylidene]-2H-pyran-2,6(3H)-dione, m.p. 196° C.

EXAMPLE 2

To a solution of 2.76 g. (0.02 mol) of m-nitroaniline in 5 ml. of pyridine cooled to 0° C. is added 3.52 g. (0.02 mol) of benzenesulfonyl chloride dropwise and the mixture is stirred for one hour at room temperature. The reaction mixture is decomposed with dilute hydrochloric acid and ice, and the solid filtered off to give m-(phenylsulfonamido)-nitrobenzene, m.p. 132°–134° C. The latter, 1.4 g. (0.005 mol), is dissolved in 100 ml. of ethanol, 300 mg. of 10% palladium-on-carbon is added and the mixture is hydrogenated in a Parr shaker. After hydrogen uptake has ceased, the catalyst is filtered off and the filtrate is used directly in the subsequent reaction. Thus the ethanolic solution (100 ml.) containing 1.2 g. (0.005 mol) of 3-phenylsulfonamidoaniline and 1.06 g. (0.005 mol) of 3,5-diacetyl-4,6-dihydroxy-2H-pyran-2-one is refluxed for one hour. The reaction mixture is concentrated and filtered to give 5-acetyl-4-hydroxy-3-[1-(3-phenylsulfonamidophenylamino)ethylidene]-2H-pyran-2,6(3H)-dione, m.p. 209° C.

EXAMPLE 3

To a hot solution of 2.12 g. (0.01 mol) of 3,5-diacetyl-4,6-dihydroxy-2H-pyran-2-one in 40 ml. of methanol is added 1.72 g. (0.01 mol) of m-sulfamylaniline and the mixture is refluxed for one hour. The solid is filtered from the reaction mixture to obtain 5-acetyl-4-hydroxy-3-[1-(3-sulfamylphenylamino)ethylidene]-2H-pyran-2,6(3H)-dione, m.p. 237° C.

EXAMPLE 4

A solution of 1.06 g. (0.005 mol) of 3,5-diacetyl-4,6-dihydroxy-2H-pyran-2-one and 0.95 g. (0.005 mol) of p-aminophenylsulfamide in 30 ml. of tetrahydrofuran is stirred overnight at room temperature. The mixture is filtered and the filtrate concentrated to give a combined yield of 5-acetyl-4-hydroxy-3-[1-(4-sulfamidophenylamino)ethylidene]-2h-pyran-2,6(3H)-dione, m.p. 221° C.

EXAMPLE 5

A solution of 2.12 g. (0.01 mol) of 3,5-diacetyl-4,6-dihydroxy-2H-pyran-2-one and 1.87 g. (0.01 mol) of m-aminophenylsulfamide in 30 ml. of tetrahydrofuran is stirred at room temperature for 48 hours. The solvent is removed, the residue treated with acetic acid and then diluted with water. The precipitated solid is filtered off and purified by high pressure liquid chromatographic separation to furnish 5-acetyl-4-hydroxy-3-[1-(3-sulfamidophenylamino)ethylidene]-2H-pyran-2,6(3H)-dione, m.p. 153°–155° C.

As a specific embodiment of a useful composition of this invention, an active ingredient such as 5-acetyl-4-hydroxy-3-[1-(3-sulfamidophenylamino)ethylidene]-2H-pyran-2,6(3H)-dione is dissolved in sterile water at a concentration of 0.5% and aerosolized from a nebulizer operating at an air flow adjusted to deliver the desired aerosolized weight of drug.

What is claimed is:

1. A compound of the formula:

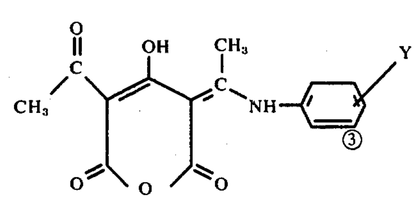

wherein Y represents sulfamyl, methylsulfonamido, phenylsulfonamido or sulfamido, or a mono-or di-alkali metal salt of said compound.

2. A compound according to claim 1 in which Y is in the 3-position.

3. A compound according to claim 2 in which Y is sulfamyl.

4. A compound according to claim 2 in which Y is sulfamido.

5. A pharmaceutical composition for inhibiting the symptoms of asthma comprising a nontoxic pharmaceutical carrier or diluent and a therapeutically effective amount to produce said inhibition of a compound of the formula:

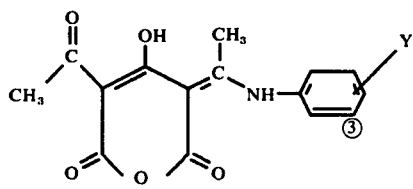

wherein Y represents sulfamyl, methylsulfonamido, phenylsulfonamido or sulfamido, or a mono-or di-alkali metal salt of said compound.

6. A pharmaceutical composition according to claim 5 in the form of a liquid suspension or solution or admixed with a solid diluent for administration by inhalation.

7. A pharmaceutical composition according to claim 5 comprising a solution or suspension of the active ingredient in sterile water.

8. A pharmaceutical composition according to claim 6 in the form of an aerosol formulation.

9. A pharmaceutical composition according to claim 5 in which the pharmaceutical carrier or diluent is a solid.

10. A pharmaceutical composition according to claim 5 in which Y is in the 3-position.

11. A pharmaceutical composition according to claim 10 in which Y is sulfamido.

12. A pharmaceutical composition according to claim 5 in dosage unit form and in which the active ingredient is in an amount of from about 2.5 mg. to about 500 mg. per dosage unit.

13. A method of inhibiting the symptoms of asthma which comprises administering to an animal in need of said inhibition a therapeutically effective amount for producing said inhibition of a compound of the formula:

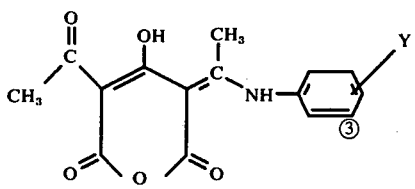

wherein Y represents sulfamyl, methylsulfonamido, phenylsulfonamido or sulfamido, or a mono-or di-alkali metal salt of said compound.

14. The method according to claim 13 in which the active ingredient is administered in a daily dosage regimen of from about 2.5 mg. to about 2000 mg.

15. The method according to claim 13 in which Y is in the 3-position.

* * * * *